Figure 1:
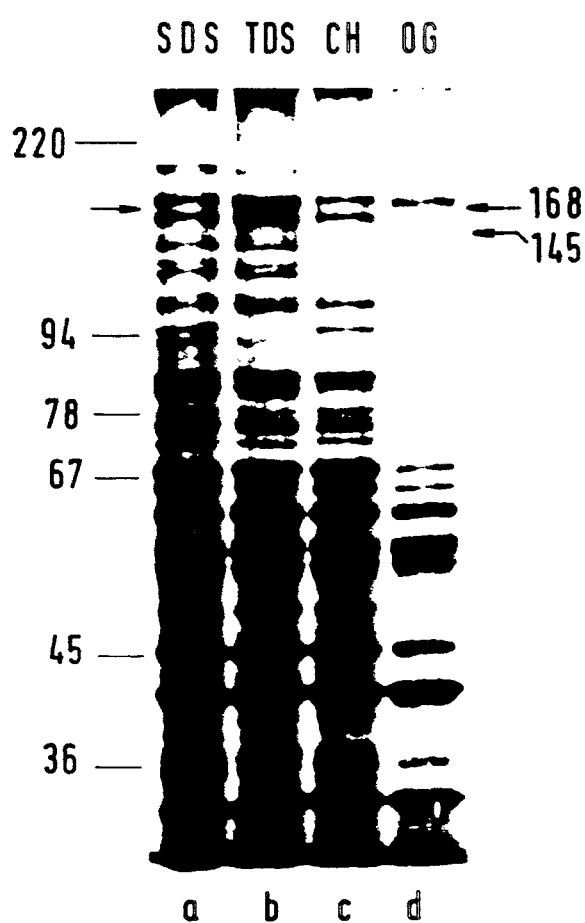

United States Patent [19]

Bredt et al.

[11] Patent Number: 5,084,561
[45] Date of Patent: Jan. 28, 1992

[54] METHOD FOR THE PURIFICATION OF A 168 KD PROTEIN FROM MYCOPLASMA PNEUMONIAE

[76] Inventors: Wolfgang Bredt; Klemens Fuchte; Enno Jacobs, all of Hoechst Aktiengesellschaft, P.O. Box 80 03 20, D-6230 Frankfurt am Main 80, Fed. Rep. of Germany

[21] Appl. No.: 326,832

[22] Filed: Mar. 21, 1989

[30] Foreign Application Priority Data

Mar. 23, 1988 [DE] Fed. Rep. of Germany ....... 3809796

[51] Int. Cl.⁵ .......................... C07K 13/00; A23J 1/00; C12Q 1/00; C12N 15/00
[52] U.S. Cl. .................................... 530/417; 530/414; 530/412; 435/7.32; 435/70.21; 435/172.2
[58] Field of Search .................... 435/272, 7.32, 70.21, 435/172.2; 530/417, 414, 412

[56] References Cited

U.S. PATENT DOCUMENTS 4,945,041 7/1990 Baseman ............................ 435/7.32

OTHER PUBLICATIONS

Laemmli, Nature, 227: 680-685 (1970).
Rollins et al., Arch. Pathol. Lab Med., 110: 34-41, (1986).
Mituzani et al., An. Rev. Respir. Dis., 127: 175-179 (1983).
Jacobs et al., Eur. J. Clin. Microbiol., 4: 113-118 (1985).
Feldner et al., Nature, 298: 765-767 (1982).
Jacobs et al., J. Clin. Microbiol., 23: 517-522 (1986).
Leith et al., J. Bacteriol., 157: 678-680 (1984).
Jacobs et al., Anal. Biochem., 154: 583-589 (1986).
Jacobs et al., Eur J. Clin. Microbiol 5: 435-440 (1986).

*Primary Examiner*—Robert A. Wax
*Assistant Examiner*—Bradley L. Sisson
*Attorney, Agent, or Firm*—Finnegan, Henderson, Farabow, Garrett, and Dunner

[57] ABSTRACT

A new method for the purification of a 168 kD protein from *Mycoplasma pneumoniae* using zwitterionic and non-ionic detergents.

18 Claims, 3 Drawing Sheets

METHOD FOR THE PURIFICATION OF A 168 KD PROTEIN FROM MYCOPLASMA PNEUMONIAE

The invention relates to a method for the purification of a 168 kD protein from *Mycoplasma pneumoniae.*

*Mycoplasma pneumoniae* causes diseases in the upper and lower respiratory tract. Up to 10% of all cases of pharyngitis, 10–30% of all cases of pneumonia in a civil population and up to about 60% of cases of pneumonia in institutionalized populations can be ascribed to this pathogen. Epidemics occur at intervals of 4–7 years, and there are also descriptions of deaths in the literature (Rollins S, et al., Arch.Pathol. Lab.Med. 110; pages 34–41 (1986)). Furthermore, many -post-infection complications such as myocarditis, endocarditis, meningitis etc., requiring etiological elucidation are known. Reinfections are not uncommon. They occur mainly in adult populations, which is the group where clinical complications are particularly to be expected.

Since *M.pneumoniae* is a bacterium and is thus, in contrast to viruses which are the predominant cause of diseases in the upper and lower respiratory tract, sensitive to antibiotics, rapid diagnosis has considerable therapeutic consequences. However, reliable differentiation of *M.pneumoniae* infection from similar viral or bacterial infections is not clinically possible. Likewise, the available laboratory diagnostic methods are unsatisfactory. Detection of the pathogen by culturing is of only confirmatory value because of the very slow growth of 1-2 weeks on exacting media. Currently, diagnosis is made by serological methods in most cases. The most widely used test, the complement-fixation test (CFT), uses a glycolipid extract from *M.pneumoniae* as antigen. However, this glycolipid shows cross-reactions both with other bacteria, for example Streptococcus MG intermedius, and with plant lipids or constituents of human cells.

False-positive CFT reactions have been described especially with diseases associated with cell destruction, for example pancreatitis, meningitis or carditis. Other test methods are too labor-intensive, such as, for example, immunofluorescence, have just as low a specificity as the CFT (ELISA with *M.pneumoniae* total extract (Mitzutani H, Mizutani H (An. Rev. Respir. Dis. 127: pages 175–179, (1983)) or can be used only in special laboratories, for example as adherence inhibition test (Jacobs E, et al., Eur.J.Clin.Microbiol. 4; pages 113–118, (1985)).

*M.pneumoniae* has in its spike structure a protein which has the molecular weight (MW) 168 kD and which is responsible for the adherence of the pathogen to the cells of the host organism (Feldner J, et al., Nature 298: pages 765–769, (1982)). It has been possible to find antibodies against this protein in all the sera that were investigated from patients infected with *M.pneumoniae,* whereas the immune response to other proteins did not occur regularly (Jacobs E, et al., J.Clin./Microbiol.23; pages 517–522, (1986a)). This 168 kD protein is thus a suitable antigen for a specific serological test.

This 168 kD protein has already been isolated using a detergent mixture composed of Triton, DOC, SDS, EDTA, Tris buffer (TDSET) and purified by immunoaffinity chromatography (Leith D. K., Baseman J. B., J Bacteriol 157; pages 678–680, Purification of a *Mycoplasma pneumoniae* adhesin by monoclonal antibody affinity chromatography, (1984)). However, the elution of the 168 kD protein which is bound to the antibodies coupled to the column in the immunoaffinity chromatography requires relatively severe conditions to dissociate the immune complex, and these may result in denaturation of the ligand and destruction of the column. A method which permits the isolation of large amounts of denatured 168 kD protein has been described by Jacobs and Clad (Jacobs E, Clad A, Anal. Biochem., 154; pages 583–589, Electroelution of fixed and stained membrane proteins from preparative sodium dodecyl sulfate-polyacrylamide gels into a membrane trap (1986)). In this study, a complete *M.pneumoniae* protein was separated by SDS-PAGE and labeled and then the band which contains the 168 kD protein was cut out of the gel and electroeluted into a biotrap system. Although it is possible with this method to isolate the 168 kD protein in amounts which can be used as antigen in a dot ELISA (Jacobs et al., Eur. J. Clin. Microbiol. 5; pages 435–440, 168-kilodalton protein of *Mycoplasma pneumoniae* used as antigen in a dot enzyme-linked immunosorbent assay (1986)), the isolation of the protein is very time-consuming, and the protein obtained by this method is not in the natural state.

Hence the object of the invention was to make available a method which makes the 168 kD protein of *Mycoplasma pneumoniae* available in adequate amounts in the natural form.

This object is achieved, based on a method for the purification of a 168 kD protein from *Mycoplasma pneumoniae,* by treating whole *M.pneumoniae* cells with a zwitterionic detergent, preferably 3-[(3-cholamidopropyl)dimethylammonio]-1-propanesulfonate (CHAPS), then extracting the 168 kD protein from the resulting pellet using a nonionic detergent, preferably octyl-β-D-glucopyranoside (octylglucoside), and finally removing other impurities by size-exclusion chromatography.

As already mentioned, Leith (1984, loc. cit.) used to dissolve the membrane proteins of *M.pneumoniae* a mixture of various detergents, containing Triton X-100, SDS and deoxycholate (TDSET). However, this mixture dissolves not only the 168 kD protein out of the membrane of *M.pneumoniae* but also contaminating high molecular weight proteins, which cannot be separated from one another by gel filtration. It was possible using the method according to the invention now to concentrate the 168 kD protein by fractional solubilization up to 20 times the amount. The remaining impurities had a significantly lower molecular weight and it was possible to remove them by a single gel filtration step. Thus, when the method according to the invention is used, it is unnecessary to expose the 168 kD protein to denaturing conditions, so that the protein can be made available in its natural form in a surprisingly large amount.

The mild conditions for the dissolution are ascribable to the nature of the detergents used. Octylglucoside is a nonionic detergent, and CHAPS is a zwitterionic detergent. Both detergents have a defined structure and an HLB of about 15. The results obtained by use of the said detergents have been compared with results obtained after the isolation of all the cellular proteins by SDS buffer or TDSET.

For the comparison, cells were treated with the dissolving buffer containing either CHAPS or octylglucoside, or with the TDSET detergent mixture. The resulting suspensions were centrifuged, and the resulting supernatant was analyzed by SDS-PAGE. The results showed that TDSET exhibits good solubility not only for molecules of relatively low molecular weight but also for the 168 kD protein and another prominent protein of the cell membrane with a molecular weight of 145 kD. As expected, it was not possible with the treatment with TDSET to separate the only slightly smaller 145 kD protein from the 168 kD protein by subsequent size-exclusion chromatography.

Octylglucoside showed a good solubility for the 168 kD protein and a lower solubility for the 145 kD protein. CHAPS does not have this property and is evidently a very efficient detergent for the solubility of the 145 kD protein but is less effective for the solubility of the 168 kD protein. The combination of the two detergents showed a surprisingly good result.

In a first step in the method, the complete cells of *M.pneumoniae* are pretreated with CHAPS, resulting in the major amount of the proteins, including the 145 kD protein and a small amount of the 168 kD protein, being dissolved. The resulting homogenate is centrifuged and then aliquots of the pellet are solubilized with various concentrations of octylglucoside.

Preferably used for the first step in the treatment of the whole cells of *M.pneumoniae* is a buffer mixture (buffer I) which contains the zwitterionic detergent CHAPS in a concentration of about 0.1–10% (w/v), preferably 1% (w/v).

The pellet obtained after the first step in the dissolution is preferably treated with the nonionic detergent octylglucoside likewise using a buffer mixture (buffer II) which contains octylglucoside in a concentration of about 0.1–10% (w/v), preferably 1–2% (w/v).

The fractional solubilization according to the invention of the 168 kD protein results in a 20-fold concentration of the desired protein compared with the amount naturally occurring in *M.pneumoniae*, which is about 1.5% of the total cellular protein. The other enormous advantage of the described method according to the invention is the fact that no other contaminating high molecular weight proteins are present. It is then possible by a single purification step by size-exclusion chromatography to separate the dissolved low molecular weight contaminating proteins from the 168 kD protein.

Besides CHAPS in a concentration of about 0.1–10% (w/v), the preferred buffer I additionally contains 100–600 mM NaCl, a complexing agent, an antireductant and a protease inhibitor in a neutral phosphate buffer, but preferably CHAPS in a concentration of about 1% (w/v), 400 mM NaCl, 1 mM EDTA, 5 mM 2-mercaptoethanol, 0.6 mM PMSF and 50 mM sodium phosphate buffer, pH 6.75. These buffer components, which are customarily used per se, assist in the stated amounts the dissolving action of the CHAPS.

Besides the nonionic detergent octylglucoside in a concentration of about 0.1–10% (w/v), the buffer II which is preferably used contains 100–600 mM NaCl, a complexing agent, an antireductant and a protease inhibitor in a neutral phosphate buffer, where the preferred concentration of the contained octylglucoside is about 2% (w/v), as well as 400 mM NaCl, 1 mM EDTA, 5 mM 2-mercaptoethanol, 0.6 mM PMSF and 50 mM sodium phosphate buffer, pH 6.75. This buffer mixture is also very suitable for the nonionic detergent octylglucoside in the present method.

In order to assist the dissolving action in the first step in the treatment of the whole cells of *M.pneumoniae*, it is possible to treat the CHAPS-pretreated cells with ultrasound, preferably for a period of 1.5 min at 0° C. The ultrasound treatment promotes the disintegration of the constituents of the cell wall, by which means the release of proteins bound to the cell wall can be enhanced.

In order to separate the homogenate produced after the treatment with CHAPS and by ultrasound into fractions, one of which contains the desired 168 kD protein, the homogenate is centrifuged, preferably for about 40 min at 25 000×g and 4° C. The desired 168 kD protein is contained in the pellet. The pellet is then washed and taken up in the buffer II described above. This can be followed by another brief ultrasound treatment.

The pellet which has been taken up in buffer II is shaken at room temperature for 5 min and subsequently centrifuged once again.

The extraction of the 168 kD protein with octylglucoside, which is contained in the buffer II, which has been carried out in this way can be followed by the resulting suspension being shaken at room temperature for about 5 minutes, which is followed in turn by centrifugation at 25 000×g for 40 mins. The resulting opaque supernatant contains the 168 kD protein and can be filtered, for example through a 0.45 μm membrane, for the subsequent size-exclusion chromatography.

The size-exclusion chromatography can preferably be carried out using a Superose 6 prep grade column. The 168 kD protein can then be eluted, in high purity, a large amount and the natural state, from this column with a SDS/sodium phosphate buffer at a pH of about 6.75.

The invention is explained in detail hereinafter by means of the figures and examples.

FIG. 1 shows a polypeptide pattern, stained with Serva blue, which was obtained after SDS-PAGE separation of the proteins from *M.pneumoniae*, the solubilization having been carried out wit various detergents.

Figure 2:
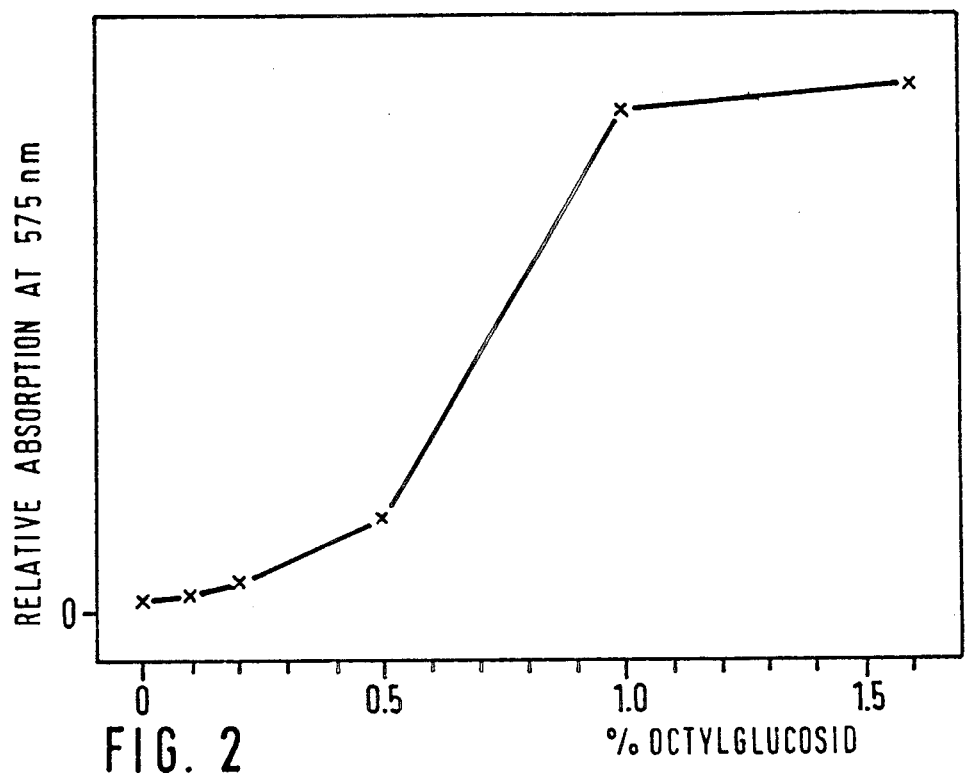

200 μg samples of cellular protein were treated with ultrasound in the presence of the particular detergent for 1.5 minutes and subsequently incubated at room temperature for a further 5 minutes. The suspensions are centrifuged at 100 000×g, and the resulting supernatants are prepared for the SDS-PAGE. The columns show a) 2% SDS
b) 1% Triton X-100, 0.2% DOC, 0.1% SDS (TDSET)
c) 1% CHAPS
d) 1% Octylglucoside FIG. 2 shows the solubilization of the 168 kD protein with various concentrations of octylglucoside.

*M.pneumoniae* cells are treated with CHAPS buffer and centrifuged, and the washed pellets (100 μg of protein each) are suspended in buffer which contains various concentrations of octylglucoside. After centrifugation, the supernatant is prepared for the SDS-PAGE, and the gel (8.25% T) is loaded. Densitomentry is carried out at 575 nm on the fixed gels which have been stained with Serva blue, and the regions of the peaks which correspond with the stained bands of the 168 kD protein are plotted against the concentration of detergent.

Figure 3:
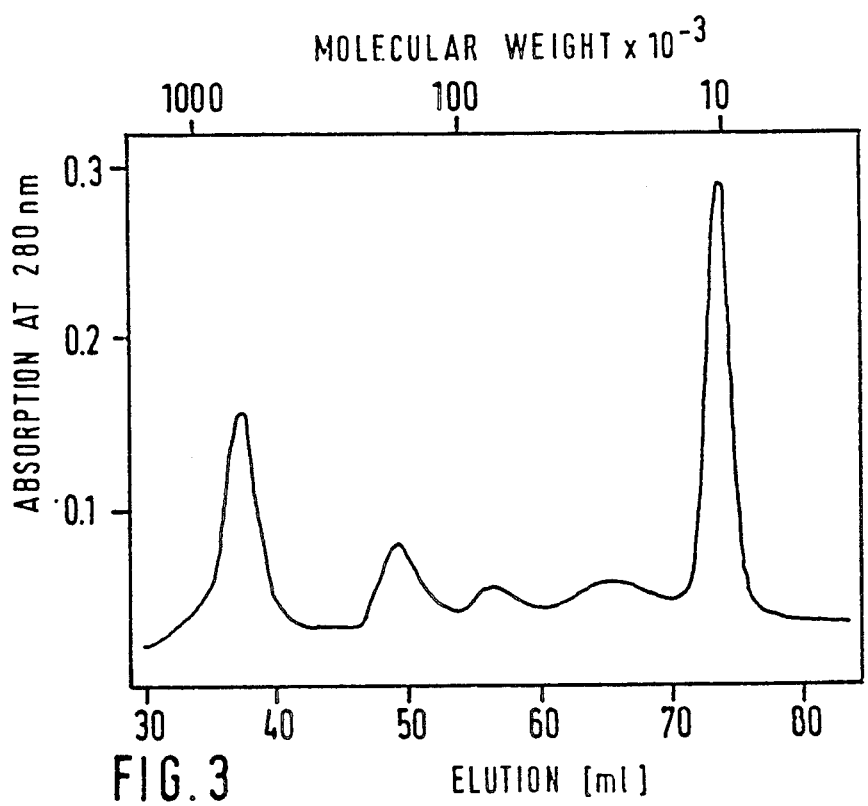

FIG. 3 shows size-exclusion chromatography of the octylglucoside solubilisate of the 168 kD protein from *M.pneumoniae*.

1 ml of octylglucoside solubilisate of the 168 kD protein is loaded onto a column (1.6×50 cm) which contains Superose 6 prep grade. 1.2 ml fractions are eluted with 0.1% SDS in 100 mM sodium phosphate of pH 6.75 at a rate of 0.2 ml/min.

Figure 4:
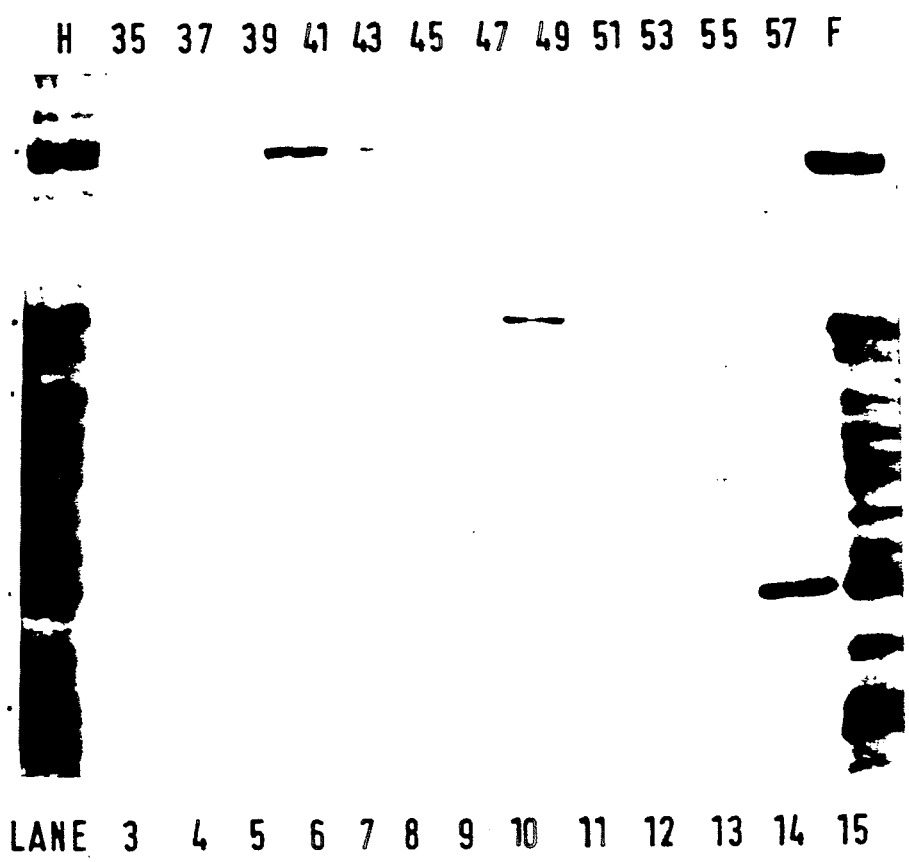

FIG. 4 shows polypeptide pattern after SDS-PAGE and staining with Serva blue of the fractions obtained by size-exclusion chromatography of the crude 168 kD protein. The experimental conditions are the same as described in FIG. 1.

Lane 2 shows total cellular protein (200 μg)
Lane 15 shows 168 kD protein
Lanes 3-14 show various fractions from the size-exclusion chromatography.

The abbreviations used throughout the description have the following meanings:

SDS Sodium dodecyl sulfate
PAGE Polyacrylamide gel electrophoresis
EDTA Ethylenediaminetetraacetate
DOC Deoxycholate
HLB Hydrophilic/lipophilic balance
TDSET Triton/DOC/SDS/EDTA/Tris buffer
CHAPS 3-[(3-Cholamidopropyl)dimethylammonio]-1-propanesulfonate
PMSF Phenylmethanesulfonyl fluoride

EXAMPLE 1

Culture of *Mycoplasma pneumoniae*

An FH strain of *M.pneumoniae* is cultured in Hayflick's medium (Hayflick L, Tex Rep Biol Med, 23; Suppl., pages 285-303, Cell cultures and mycoplasmas (1965)) in Roux bottles at 37°. The cells are harvested after 48 hours and stored at −70°.

EXAMPLE 2

Isolation of the 168 kD protein

Cells of *M.pneumoniae* prepared as described in Example 1 are suspended in 5 ml of a buffer I (1% CHAPS, 400 mM NaCl, 1 mM EDTA, 1 mM 2-mercaptoethanol, 0.6 mM PMSF, 50 mM sodium phosphate buffer with a pH of 6.75) and sonicated at 0° C. for a period of 1.5 min. The homogenate is centrifuged at 25 000×g and 4° C. for 40 min.

All the subsequent steps in the method are carried out at room temperature.

The washed pellet is resuspended in 1 ml of buffer II (2% octylglucoside, 400 mM NaCl, 1 mM EDTA, 5 mM 2-mercaptoethanol, 0.6 mM PMSF, 50 mM sodium phosphate buffer with a pH of 6.75) by brief sonication. The resulting suspension is shaken at room temperature for 5 min and then centrifuged at 25 000×g for 40 min. The opaque supernatant contains the crude 168 kD protein. The supernatant is prepared for the subsequent chromatography step by filtration through a 0.45 μm membrane (Spartan, Schleicher and Schüll, Kassel/FRG).

EXAMPLE 3

Size-exclusion chromatography

The octylglucoside solubilisate of the crude 168 kD protein is loaded onto a column (1.6×50 cm) containing Superose 6 prep grade (Deutsche Pharmacia AG GmbH, Freiburg/FRG). The elution is carried out with a flow rate of 0.2 ml/min using an elution buffer (0.1% SDS, 100 mM sodium phosphate buffer with a pH of 6.75), and 1.2 ml fractions are collected.

FIG. 3 shows an elution diagram corresponding to polypeptides with molecular weights in the range from 200 000 to 10 000. Aliquots of the fractions are analyzed by SDS-PAGE (FIG. 4). Although in some preparations the first peak, which corresponds to the exclusion volume, was up to about 10 times higher than in the chromatogram shown here, the corresponding fractions contained no protein (lane 3, FIG. 4). This absorption is presumably caused by the presence of mixed micelles in the opaque supernatant which is applied to the column. The second peak contains the well-dissolved 168 kD protein, as is evident from lanes 7 to 9 in FIG. 4. The amount of 168 kD protein which can be obtained by the method is 40% or 300 μg of 168 kD protein from 1 g of wet cell weight of the pellet.

EXAMPLE 4

SDS-PAGE

The collected protein fractions are analyzed by SDS-PAGE in 1.5 mm thick slab gels (18×14 cm) with a gel concentration of 8.75% T in a discontinuous buffer system (Laemmli U. K., Nature 227; pages 680-685, Cleavage of structural proteins during the assembly of the head of bacteriophage T4 (1970)).

EXAMPLE 5

Protein assay in dilute detergent solution

The protein is precipitated by simultaneous extraction of detergents (Wessel D, Flügge UI; Anal. Biochem. 138; pages 141-143, A method for the quantitative recovery of protein in dilute solution in the presence of detergents and lipids (1984)), and the collected protein is determined in a modification of the Lowry method (Peterson GL, Anal. Biochem. pages 346-356, A simplification of the protein assay method of Lowry et al which is more generally applicable (1977)).

COMPARISON EXPERIMENT 1

The *M.pneumoniae* cells prepared as described in the Example 1 are treated in aliquots with buffers which each contain 1% CHAPS or 1% octylglucoside or the detergent mixture TDSET (1% (v/v) Triton X-100, 0.2% (w/v) deoxycholate, 0.1% (w/v) SDS, 10 mM EDTA., 10 mM tris-HCl with a pH of 7.8), as described by Leith (1984, loc. cit.). The resulting suspensions are centrifuged, and the supernatants obtained in this way are analyzed by SDS-PAGE as described in FIG. 1.

FIG. 1 shows in lane a the polypeptide pattern obtained after SDS-PAGE and staining with Serva blue; it shows virtually all the cellular protein. The molecular weights are indicated on the left-hand edge of FIG. 1, and the position of the 168 kD protein is identified by an arrow. Lanes b to d show the polypeptide pattern of the protein fractions obtained after solubilization in the presence of TDSET or 1% CHAPS or 1% octylglucoside respectively.

It emerges that TDSET has good solution properties both for proteins of low molecular weight and for the 168 kD protein and for another essential protein of *M.pneumoniae* with a molecular weight of 145 kD. It was not possible, as shown by subsequent size-exclusion chromatography, to separate the two proteins with the molecular weights 145 kD and 168 kD from one another.

The solution properties of the detergent octylglucoside are good for the 168 kD protein but worse for the 145 kD protein. It emerges in the case of the CHAPS detergent that it is a very efficient detergent for solubilizing the 145 kD protein but has less dissolving power for the 168 kD protein.

COMPARISON EXPERIMENT 2

Determination of the effective concentration of octylglucoside

FIG. 2 shows the results obtained by treatment of the CHAPS-pretreated *M.pneumoniae* cells with a buffer II, as has been described in Example 2, containing octylglucoside in various concentrations between 0 and 2%. FIG. 2 shows that concentrations of octylglucoside above 1% suffice to solubilize the 168 kD protein. In order to ensure tolerance limits for various protein concentrations and to obtain a detergent/protein ratio of at least 5, a 2% concentration of the octylglucoside is particularly suitable, because protein concentrations up to about 4 mg/ml are then permissible.

The SDS-PAGE polypeptide pattern of the 2% octylglucoside solubilisate obtained from pellets pretreated with CHAPS is shown in lane 15 in FIG. 4.

The fractional solubilization of the 168 kD protein carried out according to the invention results in a 20-fold concentration, measured on about 1.5% of the total cellular protein of *M.pneumoniae*. These values can be obtained by densitometry. The 168 kD protein prepared as in the method according to the invention contains no contaminating high molecular weight proteins.

The fractional dissolution of the desired 168 kD protein using the steps in the method according to the invention and using the zwitterionic detergent CHAPS and the nonionic detergent octylglucoside makes an up to 20-fold concentration of the desired protein possible, with remaining impurities having a far lower molecular weight than the desired protein and thus being separable by a single gel filtration step. Thus, it is unnecessary with the method according to the invention to expose the 168 kD protein to denaturing agents, so that the protein is obtained in its natural form.

We claim:

1. A method for the purification of a 168 kD protein from *Mycoplasma pneumoniae*, comprising treating whole *M. pneumoniae* cells with a zwitterionic detergent, then extracting the 168 kD protein from the resulting pellet employing a nonionic detergent, followed by removing other impurities by size-exclusion chromatography.

2. The method as claimed in claim 1, wherein said zwitterionic detergent is 3-1-propanesulfonate (CHAPS), and said nonionic detergent is octyl-β-D-glucopyranoside (octylglucoside).

3. The method as claimed in claim 1, wherein after the treatment with said zwitterionic detergent, the cells are treated with ultrasound.

4. The method as claimed in claim 1, further comprising shaking the suspension obtained after the extraction with a nonionic detergent followed by centrifuging, and filtering the resulting supernatent which contains the 168 kD protein.

5. The method as claimed in claim 1, wherein said size-exclusion chromatography is carried out using a Superose 6 prep grade column, and the 168 kD protein is eluted with an SDS sodium phosphate buffer with a neutral pH.

6. The method as claimed in claim 2, wherein said CHAPS is present in a buffer mixture I in a concentration of about 0.1 to about 10% (w/v).

7. The method as claimed in claim 2, wherein said octylglucoside is present in a buffer mixture II in a concentration of about 0.1 to about 10% (w/v).

8. The method as claimed in claim 3, wherein the homogenate obtained after the ultrasound treatment is centrifuged.

9. The method as claimed in claim 3, wherein said ultrasound is for about 1.5 min. at about 0° C.

10. The method as claimed in claim 4, wherein said shaking is for about 5 min. at about room temperature, and said centrifugation is at about 25,000×g for about 40 min.

11. The method as claimed in claim 5, wherein said pH is about 6.75.

12. The method as claimed in claim 6, wherein said CHAPS concentration is about 1% (w/v).

13. The method as claimed in claim 6, wherein said buffer I contains about 0.1 to about 10% (w/v) CHAPS, about 100 to about 600 mM NaCl, a complexing agent, an antireductant, and a protease inhibitor in a neutral phosphate buffer.

14. The method as claimed in claim 7, wherein said octylglucoside concentration is about 1 to about 2% (w/v).

15. The method as claimed in claim 7, wherein said buffer II contains about 0.1 to about 10% (w/v) octylgulcoside, about 100 to about 600 mM NaCl, a complexing agent, an antireductant, and a protease inhibitor in a neutral phosphate buffer.

16. The method as claimed in claim 13, wherein said buffer I contains about 1% (w/v) CHAPS, about 400 mM NaCl, about 1 mM EDTA, about 5 mM 2-mercaptoethanol, about 0.6 mM PMSF, and about 50 mM sodium phosphate buffer at a pH of about 6.75.

17. The method as claimed in claim 15, wherein said buffer II contains about 2% (w/v) octylglucoside, about 400 mM NaCl, about 1 mM EDTA, about 5 mM 2-mercaptoethanol, about 0.6 mM PMSF, and about 50 mM sodium phosphate buffer at a pH of about 6.75.

18. The method as claimed in claim 8, wherein said centrifugation is for about 40 min., at about 25,000×g, and at about 4° C.

* * * * *

UNITED STATES PATENT AND TRADEMARK OFFICE
CERTIFICATE OF CORRECTION

PATENT NO. : 5,084,561

DATED : January 28, 1992

INVENTOR(S) : Wolfgang Bredt, Klemens Fuchte and Enno Jacobs

It is certified that error appears in the above-identified patent and that said Letters Patent is hereby corrected as shown below:

Col. 7: Claim 2, line 2, change "3-1-propanesulfonate" to

--3-[(3-cholamidopropyl)dimethylammonio]-1- propanesulfonate--;

Col. 8: Claim 4, line 4, change "supernatent" to

--supernatant--; and

Claim 15, line 3, change "octylgulcoside" to

--octylglucoside--.

Signed and Sealed this

Fifteenth Day of June, 1993

Attest:

MICHAEL K. KIRK

Attesting Officer

Acting Commissioner of Patents and Trademarks